United States Patent
Li

(10) Patent No.: US 10,357,434 B2
(45) Date of Patent: *Jul. 23, 2019

(54) DENTAL ROOT CANAL FILLING MATERIAL HAVING IMPROVED THERMAL CONDUCTIVE CHARACTERISTICS

(71) Applicant: TULSA DENTAL PRODUCTS LLC, Tulsa, OK (US)

(72) Inventor: Nathan Y. Li, Malibu, CA (US)

(73) Assignee: DENTSPLY SIRONA Inc., York, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/945,374

(22) Filed: Nov. 18, 2015

(65) Prior Publication Data

US 2016/0256361 A1 Sep. 8, 2016

Related U.S. Application Data

(63) Continuation of application No. 13/899,561, filed on May 21, 2013, now Pat. No. 9,192,545.

(60) Provisional application No. 61/649,899, filed on May 21, 2012, provisional application No. 61/732,839, filed on Dec. 3, 2012.

(51) Int. Cl.
*A61K 6/00* (2006.01)
*A61K 6/027* (2006.01)
*A61K 6/04* (2006.01)
*A61K 6/02* (2006.01)

(52) U.S. Cl.
CPC .......... *A61K 6/0038* (2013.01); *A61K 6/0002* (2013.01); *A61K 6/0008* (2013.01); *A61K 6/0041* (2013.01); *A61K 6/027* (2013.01); *A61K 6/0255* (2013.01); *A61K 6/04* (2013.01); *A61K 6/046* (2013.01)

(58) Field of Classification Search
CPC .. A61K 6/0038; A61K 6/0073; A61K 6/0002; A61K 6/0008; A61K 6/0041
See application file for complete search history.

(56) References Cited

U.S. PATENT DOCUMENTS

| 7,204,874 B2* | 4/2007 | Jia | A61K 6/0023 106/35 |
| 9,192,545 B2* | 11/2015 | Li | A61K 6/0038 |
| 2005/0282116 A1* | 12/2005 | Kusano | A61K 6/0038 433/224 |

FOREIGN PATENT DOCUMENTS

KR 10-2006-0086570 * 8/2006

OTHER PUBLICATIONS

Translation of KR 10-2006-0086570.*

* cited by examiner

*Primary Examiner* — C Melissa Koslow
(74) *Attorney, Agent, or Firm* — Densply Sirona Inc.

(57) ABSTRACT

A root canal filling material incorporates heat conductive particles of sub-micron size dispersed in a heat flowable matrix of endodontic filling material. The particle size is 1 micron or less (e.g., 0.5 to 1 micron, or nanoparticles of 100 nm or less). The addition of high heat conductive particles in the heat flowable matrix material improves the overall heat conductivity of the root canal filling material. During root canal treatment procedure, the filling material softens more thoroughly to fill the root canal apex and to form a seal of higher integrity at the root canal apex area, at a significantly lower operating temperature. The inventive filling material may be provided in bulk (e.g., pellet form) for use with an injection tool that heats and injects softened filling material into root canal cavities, or pre-shaped in the form of dental root canal filling cones (or points).

10 Claims, 12 Drawing Sheets

Peak shifts (in ppm of feeder frequency) of the protons of polyisoprene isomers in solution in CDCl₃ abstracted from Tskaka et al.

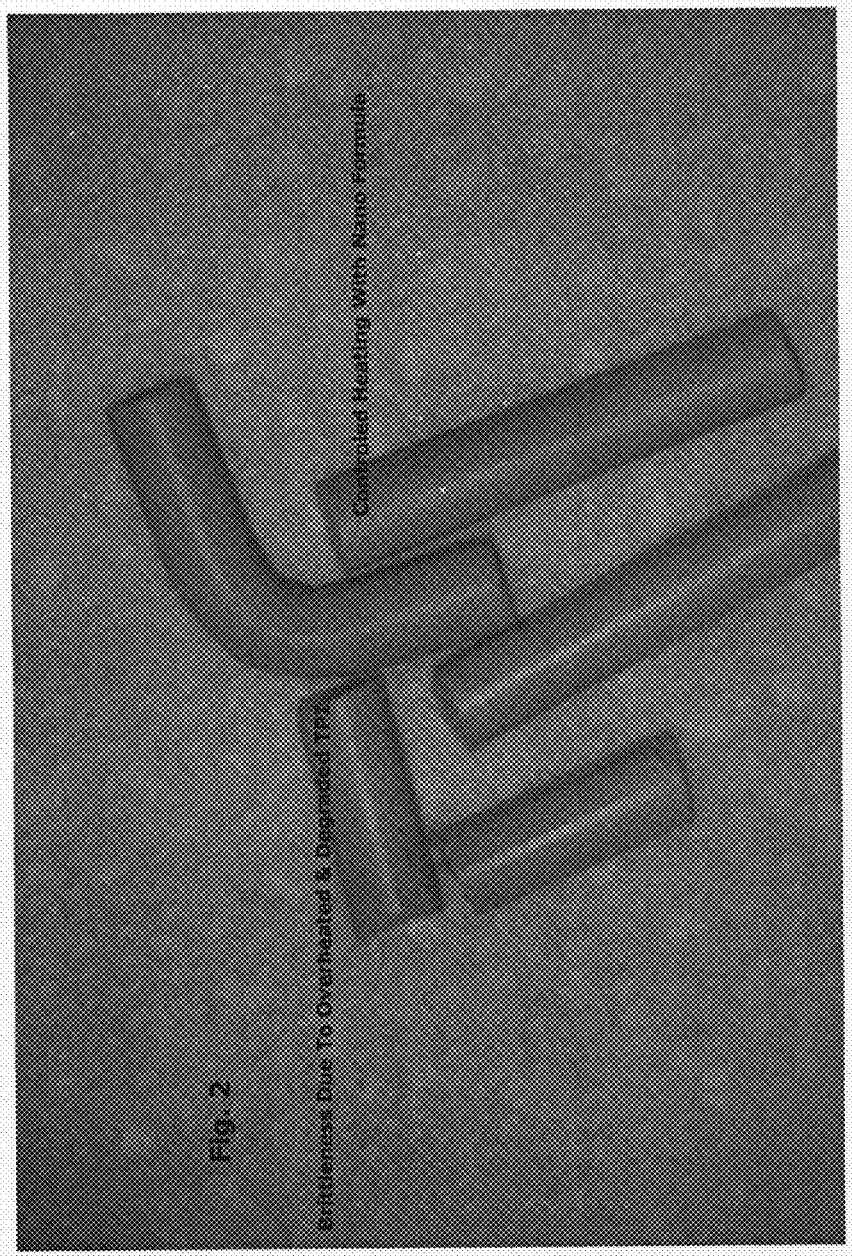

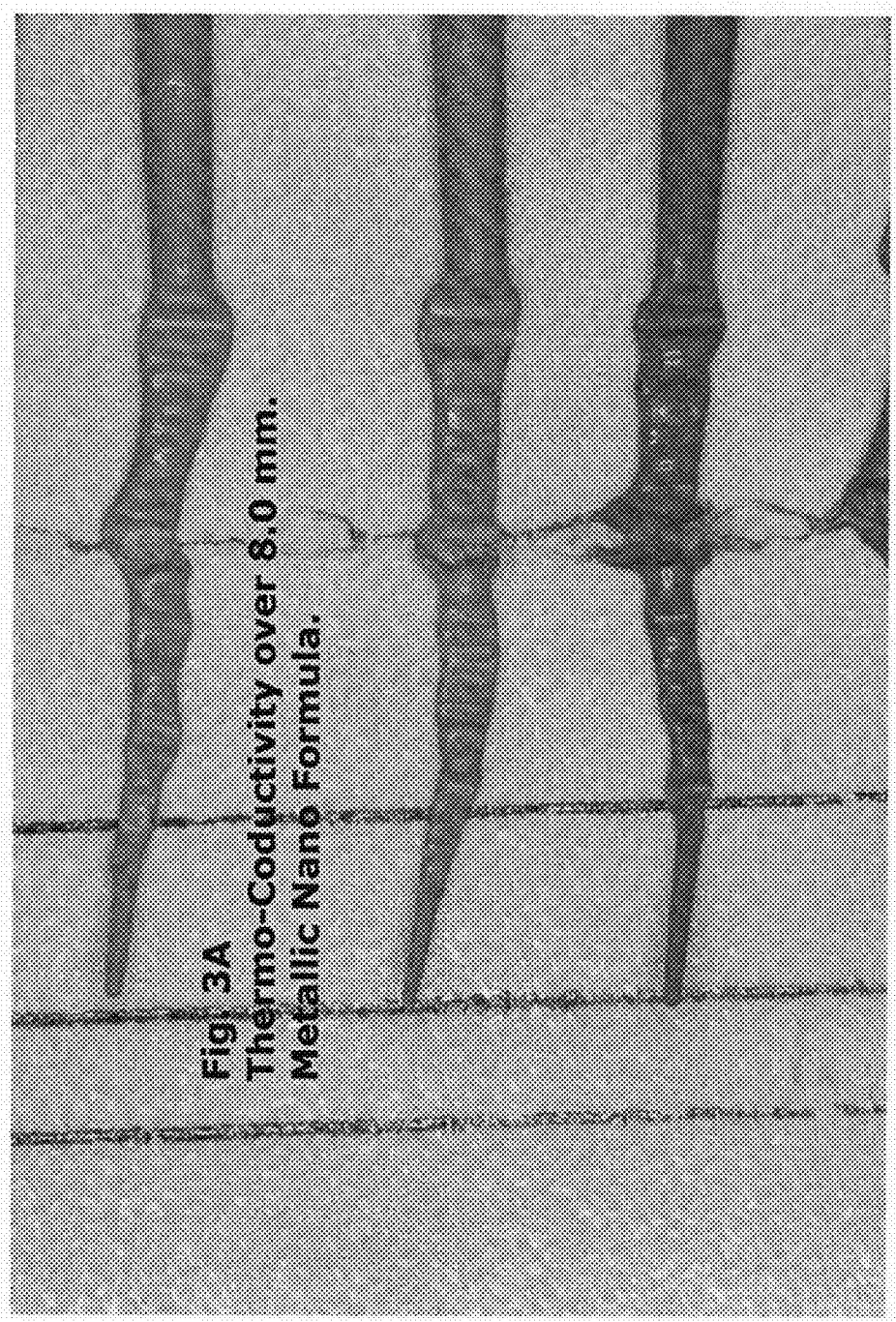
Fig. 3A Thermo-Coductivity over 8.0 mm. Metallic Nano Formula.

Thermo-Conductivity over 8.0 mm None-Metallic Nano Formula.

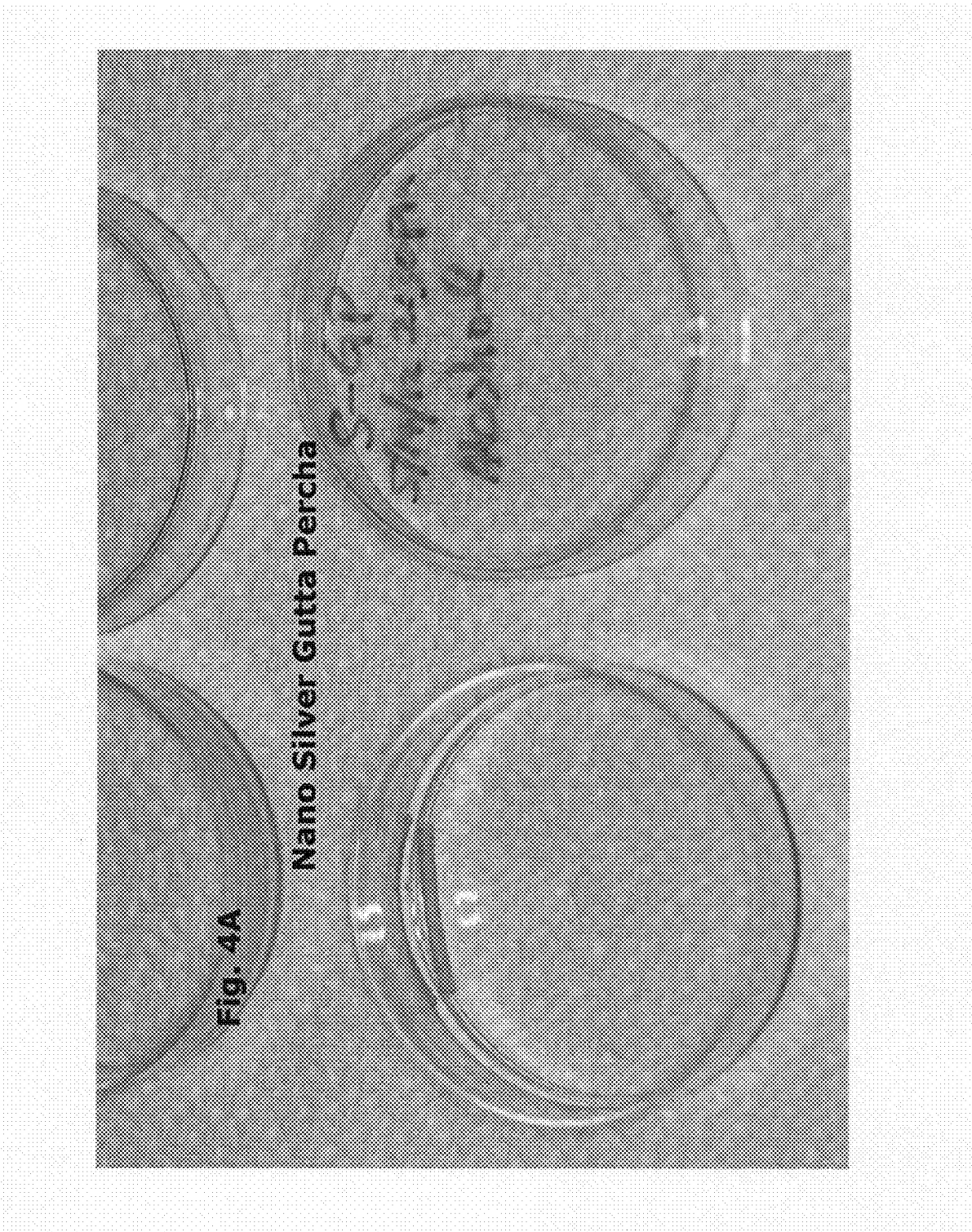

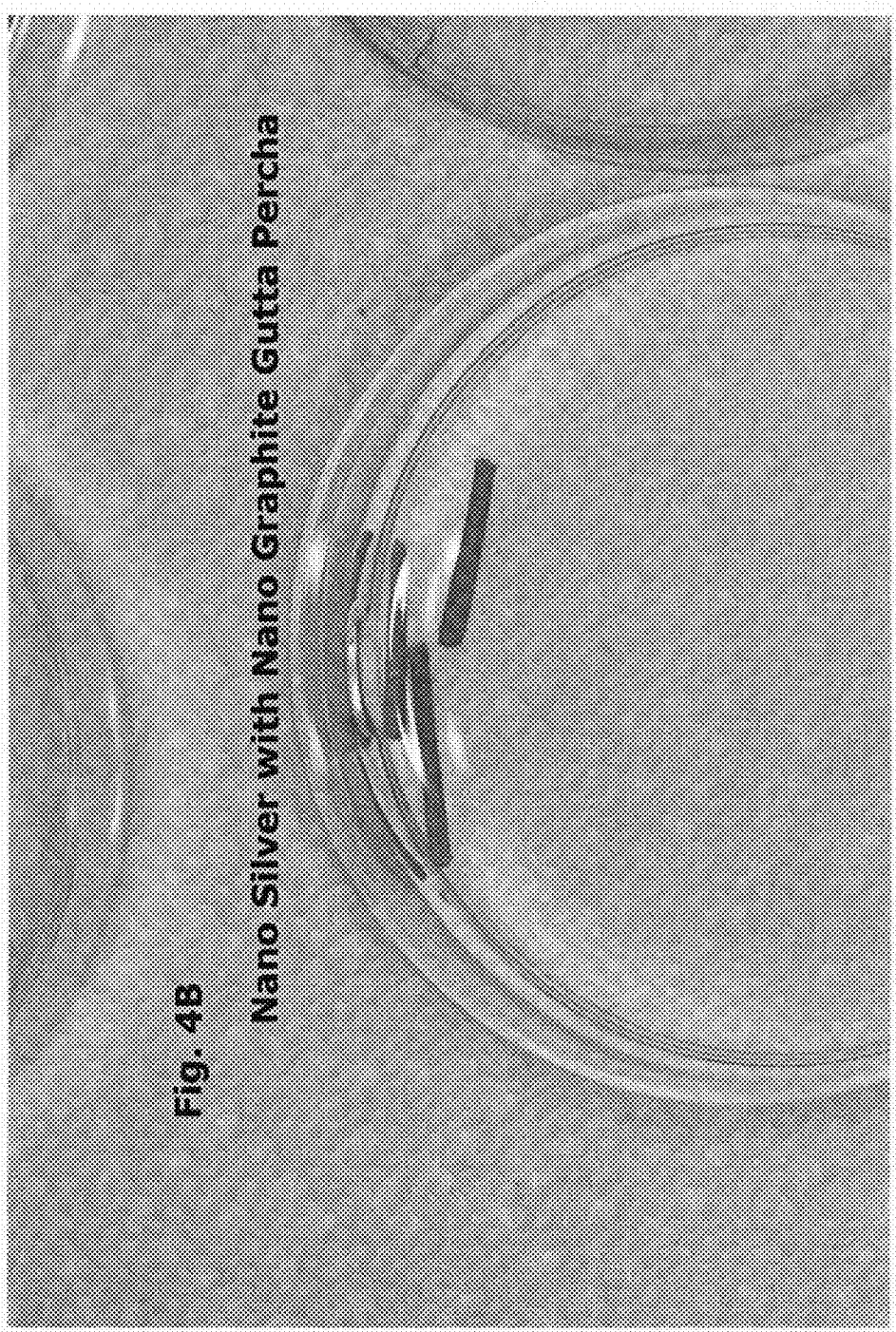
Fig. 4B Nano Silver with Nano Graphite Gutta Percha

DENTAL ROOT CANAL FILLING MATERIAL HAVING IMPROVED THERMAL CONDUCTIVE CHARACTERISTICS

PRIORITY CLAIM

This application is a continuation of U.S. patent application Ser. No. 13/899,561 filed on May 21, 2013, now U.S. Pat. No. 9,192,545, which claims the priority of U.S. Provisional Patent Application No. 61/649,899 filed on May 21, 2012, and U.S. Provisional Patent Application No. 61/732,839 filed on Dec. 3, 2012, which are fully incorporated by reference as if fully set forth herein. All publications noted below are fully incorporated by reference as if fully set forth herein.

BACKGROUND OF THE INVENTION

Field of the Invention

The present invention is directed to materials for filling dental root canals.

Description of Related Art

Dental root canal treatment generally involves three stages: shaping, cleaning and obturation (generally involving filling and sealing). The ultimate objective of root canal treatment is to eliminate the infection inside the dental root system and to tightly seal or obturate, in three dimensions (3-D), the tiny openings at the end of the root canal, (referred in the profession as an apex). Failure to completely seal the apex or the root canal in 3-D leads to micro-leakage, which will lead to future bacteria colonization inside the root canal system, and re-infection and possible loss of the tooth. Micro-leakage is the most common cause of tooth failure.

Heretofore, root canal treatment processes involve placement of a root canal filling or sealing point or cone in a prepared root canal to plug the root canal, ideally in a manner to eliminate micro-leakage. However, the existing filling points and the process of application thereof do not lend themselves well to provide a good seal of the root canal apex. Heretofore, root canal filling points are formed of a filling material that is shaped into slender cones each having a small taper angle (e.g., 5-10 degrees).

The most commonly used root canal filling material for many years is a biocompatible dry latex compound commonly called Gutta Percha (which comprises trans-polyisoprene). Zinc oxide and Barium Sulfate are fillers included in the compound. Zinc Oxide is present in an amount that provides the function of major inert filler inside dental Gutta Percha root canal filling material to improve dimensional stability. The Barium Sulfate is present in an amount that provides radio opacity of the filled root canal. Heretofore, the Zinc Oxide filler is of size on the order of greater than 50 microns. Gutta Percha molecule chains serve as a matrix supporting the inert fillers. Gutta Percha may also refer to balata and isoprene. FIG. 1 is an embodiment of the chemical structure of Gutta Percha, having the chemical composition of 1,4-trans-polyisoprene (TPI).

The following thermal mechanical characteristics of dental Gutta Percha were observed:

1. There are three crystal phases of Gutta Percha: alpha, beta and amorphous. Gutta Percha undergoes phase transitions with temperature changes. Specifically, when temperature is raised to between 42 to 49 degree Celsius, alpha phase will transition to beta phase. If temperature is raised to 53 to 59 degree Celsius, it transitions to amorphous phase. When heated Gutta Percha material is cooled at an extremely slow rate, the material will recrystallize to the phase that is stable at the lower temperature (e.g., at the alpha phase at room temperature). Otherwise if cooling is not at a slow enough rate, the material will cool to a phase corresponding to a higher temperature (e.g., at the beta phase). Natural Gutta Percha is mostly in the alpha phase, and dental Gutta Percha is mostly in the beta phase due to the heat treatment the Gutta Percha material was subject to during the manufacturing process of dental Gutta Percha filling points.

2. During a root canal treatment procedure, temperature is necessarily raised to soften the Gutta Percha material to fill the root canal. The temperature is raised above the threshold to cause the material to transition to the amorphous phase, so as to flow the material to fill the root canal. Thereafter, given it is difficult to control the cooling rate, the Gutta Percha material will normally cool to the beta phase, resulting in shrinkage in volume after the root canal treatment procedure, which leads to potential micro-leakage problem.

3. Given dental Gutta Percha material is a rather poor thermal conductor, and further coupled with heat dissipation by the patient's jaws, it has been known that heat is not effectively conducted to soften the material beyond about 3.0 mm from a reasonable heat source. This will prevent having softened Gutta Percha forming a perfectly fitted plug at the root canal apex area to provide a 3-D seal to prevent micro-leakage.

Currently, most dentists use a heated probe to soften and to push dental Gutta Percha cones/points into root canals, by a technique known as Warm Gutta Percha technique. Most of the time, the probe temperature is set at significantly above the Gutta Percha phase change temperature threshold. This will induce crystal phase change; therefore shrinkage will occur upon cooling. One way to counter this is to use the probe to apply pressure on the Gutta Percha material in the root canal while the material is being cooled. In order to have a perfect 3-D seal at root canal apex area, dentists like to push the heat probe as deep into the root canal as possible to soften the distal tip of Gutta Percha cone. Because the dental root structure at the apex area is rather thin and to avoid burning tissue outside the apex area by the heated probe, dentists are not supposed to push the heat tip within 5 mm from the root canal apex. Given that dental Gutta Percha can only conduct heat wave no more than 3 mm at its best, the tip portion of the Gutta Percha cone is not softened to seal the apex portion of the root canal. Therefore a perfect 3-D seal in not achieved.

There is a system on the market today which could introduce pre-heated/pre-softened Gutta Percha into apex area via a solid carrier. The problem with this approach is that this solid carrier has to permanently stay inside the root canal system as part of the final seal. When root canal retreatment is needed, this solid carrier may not be effectively removed to regain access to the apex area of the root canal.

Attempting to satisfy dentists' clinical needs to have a perfect 3-D seal at root canal apex, manufacturers today are trying to lower Gutta Percha's viscosity (using Mooney indexing machine for measurement), so as to increase Gutta Percha's flowability for better 3-D molding when softened with heat. During the manufacturing process, to lower Gutta Percha's viscosity and increase its flowability, the dental Gutta Percha compound is subject to much higher heat treatment for extended time period. Gutta Percha molecule chain is a low temperature latex material. When it is subject to very high temperature, it is degraded, carbonated, and evaporated. When this happens, dental Gutta Percha compound loses its matrix and becomes a very dry and brittle mass, which will make potential micro leakage even a bigger possibility. Some manufacturers try to add a significant dose of mineral wax at the end of heat treatment to facilitate bonding of inert fillers together inside the dental Gutta Percha compound. Problems with using excessive wax are: (1) Wax evaporates even easier under heat and will leave voids in the root canal filling material. (2) Wax oxidizes very easily to cause the entire dental Gutta Percha compound to break down with much shorter shelf-life.

It can be seen that the current root canal treatment procedures involve complex and challenging steps, which may still result in micro-leakage. It would be desirable to develop an improved root canal filling material to facilitate the root canal treatment procedure to improve treatment success rate.

SUMMARY OF THE INVENTION

The present invention provides an improved root canal filling material that result in better obturation with less micro-leakage. The inventive root canal filling material has improved thermal mechanical properties, which reduces the operating temperature for root canal treatment procedures (e.g., from 200 degrees Celsius to 145 degrees Celsius, or lower), produces slight dimensional expansion instead of shrinkage during cooling period, increases density to reduce air bubble voids during heating-cooling cycle, and ultimately improving the treatment success rate to preserve more healthy teeth for a longer period of time.

In one aspect of the present invention, the inventive root canal filling material comprises heat conductive particles of sub-micron size dispersed in a base matrix of heat flowable endodontic filling material. The particles are preferably bio-inert, which may be organic or inorganic, or a combination or mixture of both. The shape of the particles may be regular, irregular, symmetrical or non-symmetrical, having random or specific geometrical shapes (e.g., spherical, ellipsoidal, rhomboidal, disc, hollow or exotic shapes). The surface of the particles may be finished, e.g., polished, matte, or coated.

The characteristic size (or the statistical average size) of the particles is on the order of 1 micron or less. In one embodiment, the characteristic size is 0.5 to less than 1 micron. In another embodiment, the characteristic size is on the order of 100 nm or less, in the nanoparticle range. The characteristic size of the particles does not have to be uniform. All particles may be generally or substantially the same size, or have random sizes within the prescribed size range.

The particles may be made of high heat conductive metal, non-metal, organic or inorganic materials, including without limitations Zinc Oxide, Magnesium Silicate, gold, silver, titanium, diamond, etc. The matrix of base filling material may include natural or synthetic heat flowable polymeric materials that are bio-inert or bio-compatible when disposed in dental root canals, which may include rubber, thermoplastic or other polymeric materials. Rubber material may include trans-polyisoprene based material, such as Gutta Percha. In a specific embodiment, metallic nanoparticles are dispersed in dental Gutta Percha material.

The addition of high heat conductive particles in the base matrix of heat flowable material improves the overall heat conductivity of the root canal filling material. The filling material may be softened more thoroughly to fill the root canal apex and to form a seal of higher integrity at the root canal apex area, and the root canal treatment procedure can be undertaken at a significantly lower operating temperature.

The inventive filling material may be provided in bulk (e.g., pellet form) for use with an injection tool that heats and injects softened filling material into root canal cavities. In another aspect of the present invention, pre-shaped dental root canal filling cones (or points) are formed with the inventive root canal filling material.

BRIEF DESCRIPTION OF THE DRAWINGS

For a fuller understanding of the nature and advantages of the invention, as well as the preferred mode of use, reference should be made to the following detailed description read in conjunction with the accompanying drawings. In the following drawings, like reference numerals designate like or similar parts throughout the drawings.

FIG. 2 illustrates comparison of bending of prior art Gutta Percha material and root canal filling material in accordance with the present invention.

FIG. 3A and FIG. 3B are comparison heat conductivity experiment of two types of filling material incorporating metal and non-metal nanoparticles.

FIG. 4A and FIG. 4B illustrate experiments testing corrosion of filling materials in accordance with the present invention.

DETAILED DESCRIPTION OF THE PREFERRED EMBODIMENTS

This invention is described below in reference to various embodiments with reference to the figures. While this invention is described in terms of the best mode for achieving this invention's objectives, it will be appreciated by those skilled in the art that variations may be accomplished in view of these teachings without deviating from the spirit or scope of the invention.

The present invention provides an improved root canal filling material that result in better obturation with less micro-leakage. The inventive root canal filling material has improved thermal mechanical properties, which reduces the operating temperature for root canal treatment procedures, produces slight dimensional expansion instead of shrinkage during cooling period, increases density to reduce air bubble voids during heating-cooling cycle, and ultimately improving the treatment success rate to preserve more healthy teeth for a longer period of time.

In one aspect of the present invention, the inventive root canal filling material comprises heat conductive particles of sub-micron size dispersed in a base matrix of heat flowable endodontic filling material. The present invention will be described herein-below in reference to root canal filling cones made of base endodontic filling material including what is known as Gutta Percha. However it is understood that the present invention could be applied to form root canal filling points based on other types of base endodontic filling materials, currently known or future discovered, without departing from the scope and spirit of the present invention.

According to the present invention, a composite root canal filling material is developed, wherein the heat conductivity of the root canal filling material is improved by addition of high heat conductive material in a relatively low heat conductive root canal filling material. In one aspect of the present invention, high heat conductive particles are dispersed in the root canal filling material to result in a root canal filling material having an overall high heat conductivity property. The heat conductivity of the particles is significantly higher than the heat conductivity of the heat flowable matrix material.

Figure 10:
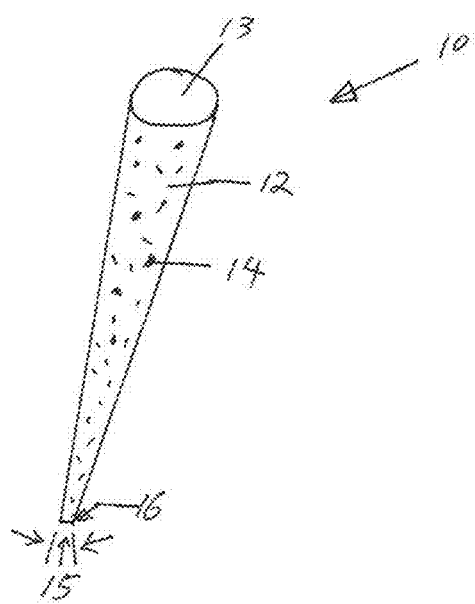
FIG. 10 is a schematic illustration of a root canal filing cone in accordance with one embodiment of the present invention.

FIG. 10 illustrates a dental root canal filling cone (or point) 10 in accordance with one embodiment of the present invention. The cone 10 comprises a generally conical body comprising a heat flowable matrix 12 and heat conductive particles 14 dispersed in the matrix 12. The cone 12 has a larger end 13 and a tapered end 16, which has a taper angle 15 that fits in the apex end of a prepared root canal cavity (the taper angle at the apex of the cavity being defined using a file tool known in the dentistry field). During a dental root canal treatment process, the cone 10 is inserted into the prepared root canal cavity, and heat is applied to the large end 13 using a heating tool (e.g., a heat gun). As the matrix 12 softens under the applied heat, the matrix material flows in the root canal cavity to fill the root canal. Ideally, sufficient heat reaches the small end 16 of the cone 10 to flow the matrix material to completely fill the apex of the root canal cavity. The present invention facilitates heat conduction to the small end of the cone.

The particles 14 may be made of high heat conductive metal, non-metal, organic or inorganic materials, including without limitations Zinc Oxide, Magnesium Silicate, graphite, gold, silver, titanium, diamond, etc. The matrix 12 of base filling material may include natural or synthetic heat flowable polymeric materials that are bio-inert or bio-compatible when disposed in dental root canals, which may include rubber, thermoplastic or other polymeric materials. Rubber material may include trans-polyisoprene based material, such as Gutta Percha.

In a specific embodiment, the particles 14 may include metallic nanoparticles dispersed in a matrix 12 of dental Gutta Percha material as the endodontic filling material. In one embodiment, the nanoparticles are metallic (e.g., titanium, silver, gold, etc.) or non-metallic (e.g., diamond, Zinc Oxide, Magnesium Silicate, graphite, etc.). By improving the overall heat conductivity of the filling material, the filling material may be softened more thoroughly to fill the root canal apex and to form a seal of higher integrity at the root canal apex area, and the root canal treatment procedure can be undertaken at a significantly lower operating temperature.

The particles are preferably bio-inert, which may be organic or inorganic, or a combination or mixture of both. The shape of the particles may be regular, irregular, symmetrical or non-symmetrical, having random or specific geometrical shapes (e.g., spherical, ellipsoidal, rhomboidal, disc, hollow (e.g., tube shaped), U-shaped, slender body shaped (e.g., rod-shaped), or other geometrical or non-geometrical shapes). The surface of the particles may be finished, e.g., polished, matte, or coated.

The characteristic size (or the statistical average size) of the particles is substantially on the order of less than 1 micron (for generally spherical particles, size refers generally to the diameter of the particles; for particles of other 3D geometrical shapes that is not slender body, size refers to the average center sectional dimension; for particles having a generally slender body (e.g., a tube or rod shaped body), size refers to the largest dimension of the body). The characteristic size of the particles does not have to be uniform within the matrix material. All particles may be generally or substantially the same size, or have random sizes within the prescribed size range.

In one embodiment, the characteristic size is substantially on the order of 100 nm or less, in the nanoparticle range. According to nano-technology, nanoparticles exhibit properties that are not found in bulk samples of the same material. At the nano-scale, the physics of nanoparticles is such that their properties are different from the properties of the same material in larger, bulk form. For purpose of the present invention, nanoparticles are particles have a characteristic size (or critical dimension) substantially no greater than 100 nm. As noted earlier, the inventive root canal filling material having nanoparticles has improved thermal mechanical properties, which reduces the operating temperature for root canal treatment procedures, produces slight dimensional expansion instead of shrinkage during cooling period, increases density to reduce air bubble voids during heating-cooling cycle, and ultimately improving the treatment success rate to preserve more healthy teeth for a longer period of time. The advantages of the inventive root canal filling material is further elaborated below.

In the past, various metallic and non-metallic materials have been accepted for use in dentistry. For example, titanium is being used for dental implants and pure silver cones, Zinc Oxide and Magnesium Silicate have been used as another type of root canal filler (without Gutta Percha material). In accordance with the present invention, these types of metallic and non-metallic material biocompatible materials are incorporated into dental Gutta Percha material to significantly change its thermal mechanical properties. For example, when producing by compounding traditional dental Gutta Percha material, the temperature required for this process is around 370 degrees Fahrenheit. In accordance with the present invention, with heat conductive material (e.g., metallic) powder added during the compounding process, the processing temperature requirement can be reduced to 140 degrees Fahrenheit. According to tests conducted, nanoparticles, as compared to larger particles, would provide better thermal mechanical characteristics for purposes of root canal filling points. It has been found that larger metallic particle sizes are more difficult to be incorporated homogenously into dental Gutta Percha material. Larger metallic particles along with poorly incorporated Gutta Percha material showed only limited improvement of heat conductivity. In one embodiment, it has been found that nano-size particles work better to improve the thermal mechanical characteristics of the base matrix of dental Gutta Percha material. Further, by incorporating different sizes and/or different types of nano particles (e.g. 30 nm, 70 nm, & 100 nm), metallic and non-metallic, to be incorporated into dental Gutta Percha compound, it has been found that such could further improve the thermal mechanical characteristics of the heat flowable matrix compound. For example, silver nanoparticles and Zinc Oxide nanoparticles are added to a matrix of dental Gutta Percha material to form a composite root canal filling material. Silver and Zinc Oxide nanoparticles in powder form are commercially available, with particle sizes in 100 nm, 75 nm, 50 nm, and 20 nm. Other sizes of nanoparticles could also work in accordance with the present invention.

The addition of high heat conductive particles in the base matrix of heat flowable material improves the overall heat conductivity of the root canal filling material. The filling material may be softened more thoroughly to fill the root canal apex and to form a seal of higher integrity at the root canal apex area, and the root canal treatment procedure can be undertaken at a significantly lower operating temperature.

Preliminary tests indicated that nanoparticle size at 100 nm or less are easier to be incorporated into dental Gutta Percha material and showed far superior heat conductivity at much lower applied temperature during the root canal treatment procedure. Because heat travels further within nanoparticle enhanced dental Gutta Percha compound, dentists no longer need to insert heating probes deep into the root canal to soften Gutta Percha compound at apex area for a better 3-D oburation. This avoids the risk of burning healthy live tissue outside apex area.

Figure 1:
FIG. 1 is a representation of the chemical structure of one embodiment of Gutta Percha material.
Figure 3B:
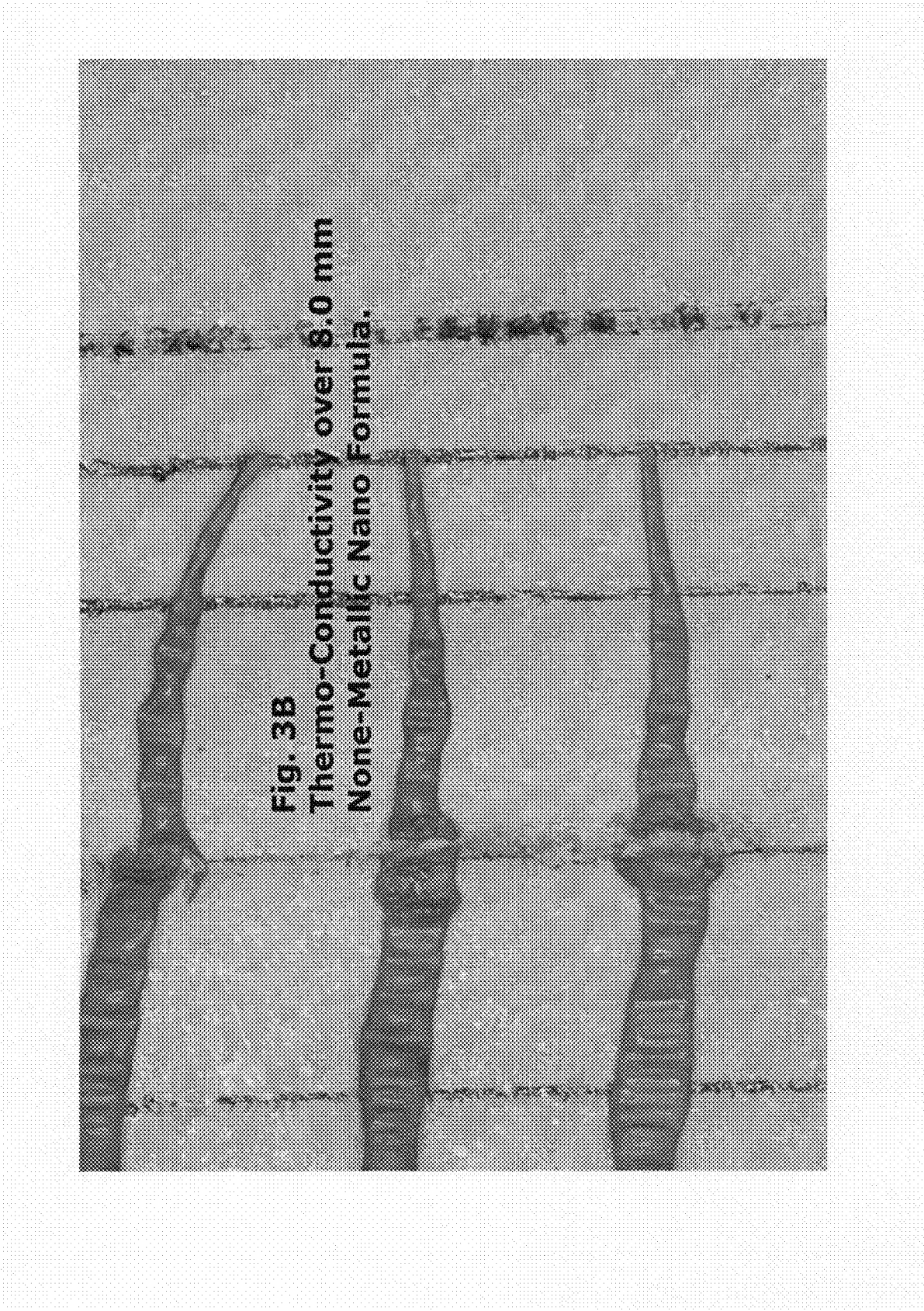

Referring to experimental results shown in FIGS. 3A and 3B, FIG. 3A shows the heat conductivity test with root canal filling cones having metallic nano particles in Gutta Percha material in accordance with the present invention. The first vertical line on the right is the 0 mm reference mark where a 135 degrees Celsius heat source had been applied to soften the Gutta Percha cones. The second line to the left is the 5 mm mark, and the third line to the left is the 8 mm mark. FIG. 3B show the heat conductivity test with root filling cones having non-metallic nanoparticles in Gutta Percha material in accordance with the present invention. The second vertical line from left is the 0 mm reference mark where a 135 degrees Celsius heat source had been applied to soften the Gutta Percha cones. The third line from left is the 5 mm mark and the fourth line from left is the 8 mm mark. Both FIGS. 3A and 3B show that dental Gutta Percha cones having nanoparticles all have heat conductivity beyond 5 mm mark. And they also further show that by adding different type, amount, and size of nano particles, heat conductivity can be manipulated accordingly.

To improve dental Gutta Percha material heat conductivity even further, it has also been found that sub-micron scale particles of varying sizes can be added to result in broader spectrum of thermal mechanical properties of the root canal filling material. Sub-micron particles are defined as particle sizes smaller than one micron. In one embodiment, sub-micron particle size is substantially within the range of 0.5 nm to less than 1 micron. The amount of metallic powder being added into dental Gutta Percha material affects overall heat conductivity of the root canal filling point. Although there is a linear relationship between the percentage of metallic powder added into dental Gutta Percha material and the degree of increase in heat conductivity, adding too much metallic powder will result in the Gutta Percha material taking in too much heat too fast during the dental Gutta Percha production cycle. This may cause fast and/or unstable crystal phase change, which may lead to excessive shrinkage after cooling.

Another advantage of using nano-sized metallic particles, in addition to enhancing dental Gutta Percha heat conductivity and to lowering overall Gutta Percha "melting temperature" threshold, is overcoming the age-old issues of corrosion and leakage caused by older generation of pure metallic and Zinc Oxide root canal filling materials used for root canal treatment. The classic example would be silver point used for root canal treatment. The known living bacteria are far bigger than nano sized metallic particles. For example, one of the smallest bacteria, Whooping Cough bacteria is 0.25 micron in diameter, which is 12.5 times bigger than a 20 nanometer silver particle. Based on preliminary tests, there is no separation/corrosion of nano sized metallic particles from dental Gutta Percha compound after submerging the sample into saline and alcohol for over 1500 hours. FIG. 4A shows the experiment with Gutta Percha having silver nanoparticles, and FIG. 4B shows the experiment with Gutta Percha having silver nanoparticles and graphite nanoparticles.

Generally, it has been found that if the particle sizes are too big, it will be more difficult to a homogenous mix with the Gutta Percha matrix. As a result, it will reduce the flowability of dental Gutta Percha material, as it becomes too brittle, and less penetration into small dentinal tubules naturally existed in the dental root structure. As the end result, it will be less seal, and more potential micro-leakage. If particle sizes are small, it will more homogenously mix with Gutta Percha. It will result in better thermal conductivity and flowability, therefore will seal small dentinal tubules better. However, if the percentage of the small size particles are too high, the dental Gutta Percha compound will become too dense. It will reduce flowability and heat conductivity. It will be very brittle as well. At the end, it will be more challenging to have a perfect seal in root canal system. The best approach is to incorporate particles with a mix of micron, sub-micron, and nano sizes. This will achieve most homogenous mix with Gutta Percha matrix, and will provide better heat conductivity, flow ability, elasticity, and less shrinkage. At the end, will be a better seal. It has been found that it is acceptable to have particles of sub-micron and nano sizes in accordance with the present invention up to 30% of total fillers present in the matrix (i.e., there are 70% of other fillers such as those found in traditional dental Gutta Percha materials).

Known traditional rolling process of forming root canal filling points (e.g., hand rolling or machine rolling) can take advantage of the inventive root canal filling material, which incorporates metallic and/or non-metallic nanoparticles mixed into a matrix of dental Gutta Percha material. In the past, the process of preparing dental Gutta Percha material for forming filling points involves oven preheating of dental Gutta Percha to break up long molecule chains. After preheating, the Gutta Percha compound mixing process is undertaken. At this point, a small quantity of mild acid is added into mixing process to further break up Gutta Percha molecule size. These "breakup" processes will produce a lot of heat, thus molecular crystal phase will transition back and forth many times, thereby introducing instability into the dental Gutta Percha compound. In accordance with the present invention, when nano sized metallic powder is added into the dental Gutta Percha material, oven preheating of the Gutta Percha material is no longer needed. And the amount of acid required is greatly reduced when nano sized metallic particles are slowly added at this stage of mixing/compounding. As a result, significantly less heat is generated during the process of forming the root canal filler point. Given less heat generated during the forming process, the Gutta Percha molecule chain is better preserved as matrix to hold inert fillers together as compound. The resultant root canal filling point formed by the process is more stable with respect to the Gutta Percha crystalline phase. It becomes less brittle therefore less shrinkage after cooling (FIG. 2). Because Gutta Percha expands when heated and nano particles preserved more Gutta Percha molecule chains during compounding process, this newly developed dental Gutta Percha material expand slightly instead of shrink after cooling.

Figure 5:
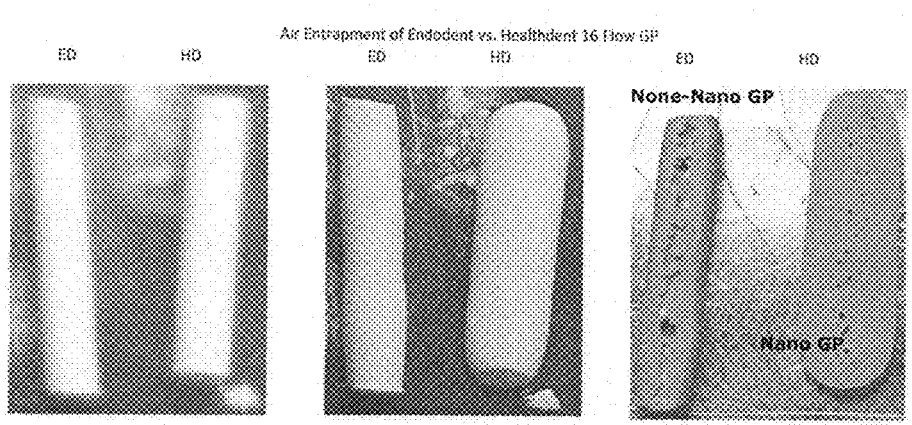
FIG. 5 shows comparisons between a conventional pellet of filling material and a pellet of filling material in accordance with the present invention.

FIG. 5 shows comparison heat treatment of dental Gutta Percha filling materials with and without nanoparticles. The left frame shows two Gutta Percha pellets sitting on a heat plate before getting heated. On the left is a conventional prior art pellet not having nanoparticles and on the right is a pellet formed of the inventive filling material that includes nanoparticles in accordance with the present invention. The middle frame shows the result after heating reached 200 degrees Celsius, when the inventive Gutta Percha pellet on the right side expands more than the prior art Gutta Percha pellet. The right frame shows the results after the Gutta Percha pellets cooled down to room temperature, and are cut in half. It shows the inventive Gutta Percha pellet on the right has less air bubble trapped inside than the prior art pellet on the right. As FIG. 5 demonstrates, given nano particle enhanced dental Gutta Percha has less trapped air bubbles or voids during heating and cooling cycle, less clearance would be available for bacteria to develop. This is due to increased density of the nanoparticle enhanced compound.

Figure 6:
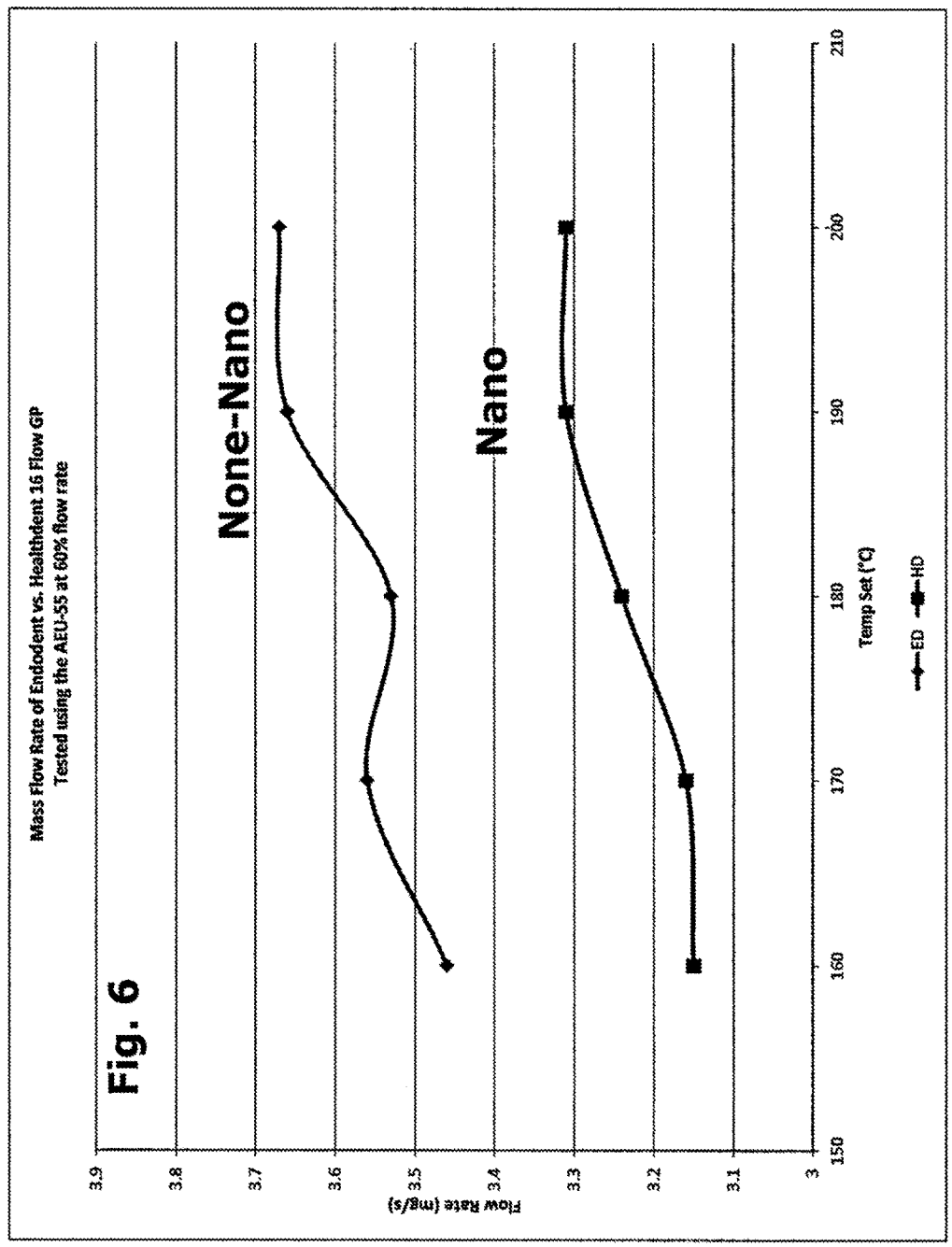
FIG. 6 shows mass flow rate vs. temperature for conventional filling material and the inventive filling material.
Figure 7:
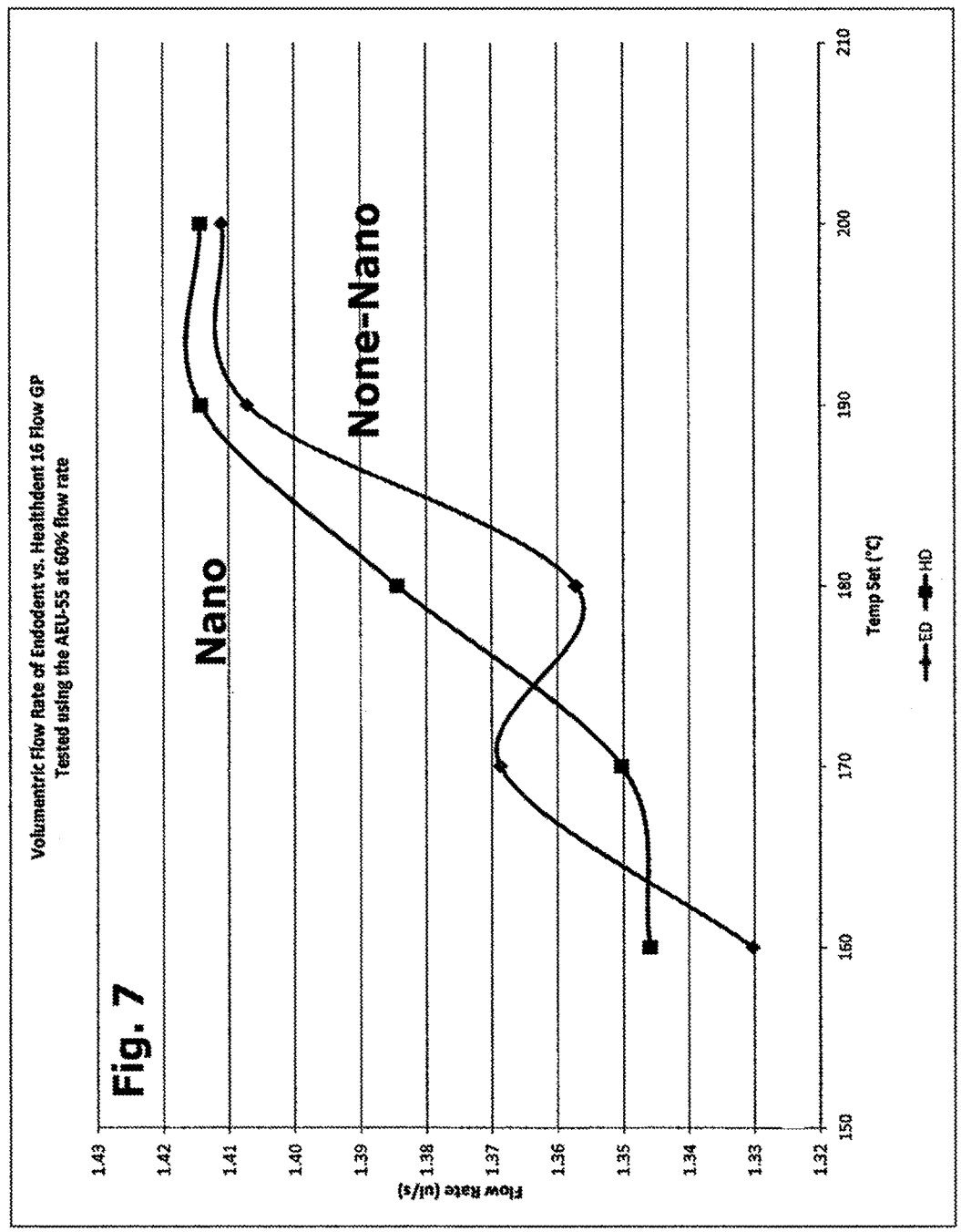
FIG. 7 shows volumetric flow rate vs. temperature for conventional filling material and the inventive filling material.
Figure 8:
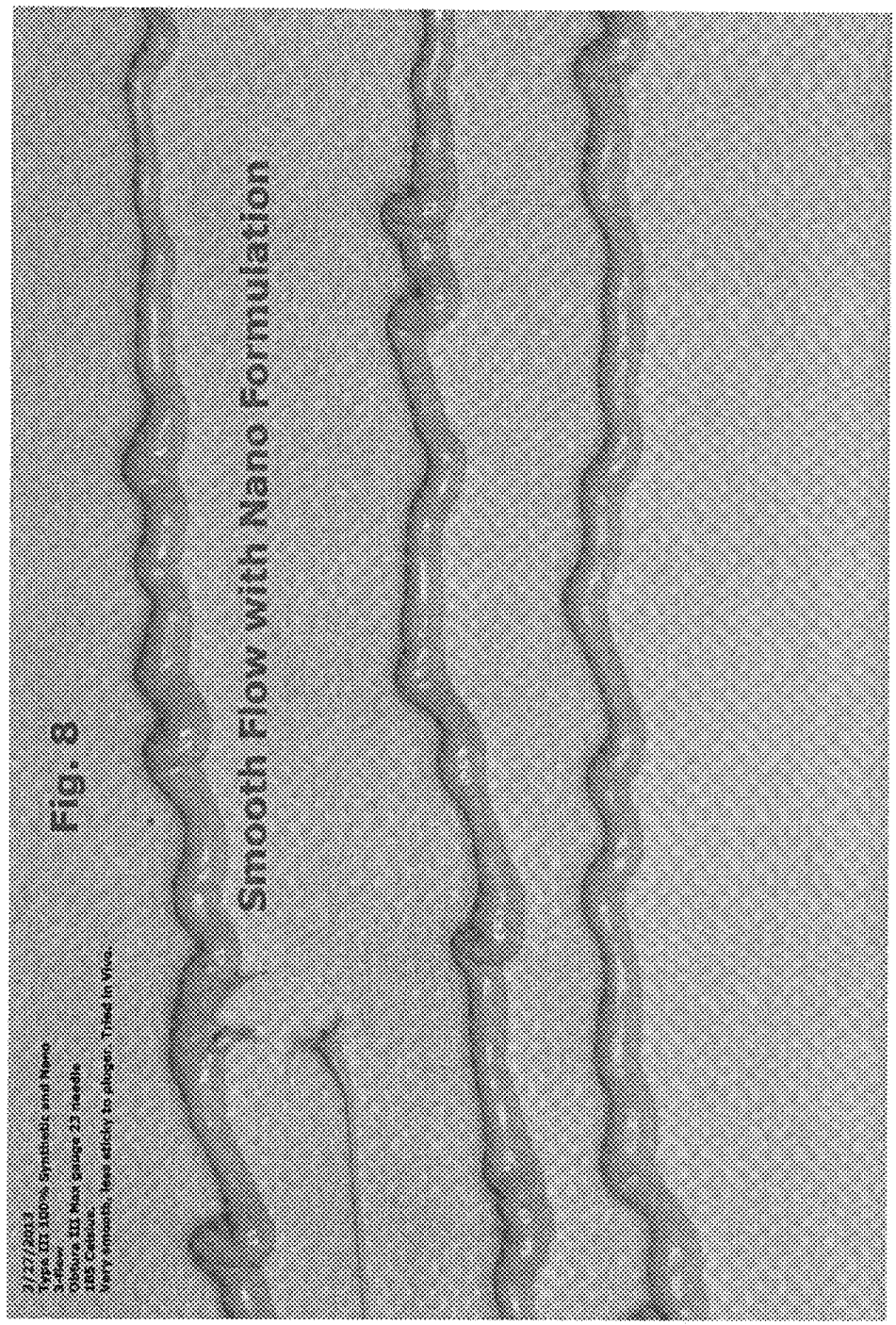
FIG. 8 illustrates smoother surface for inventive filling material.
Figure 9:
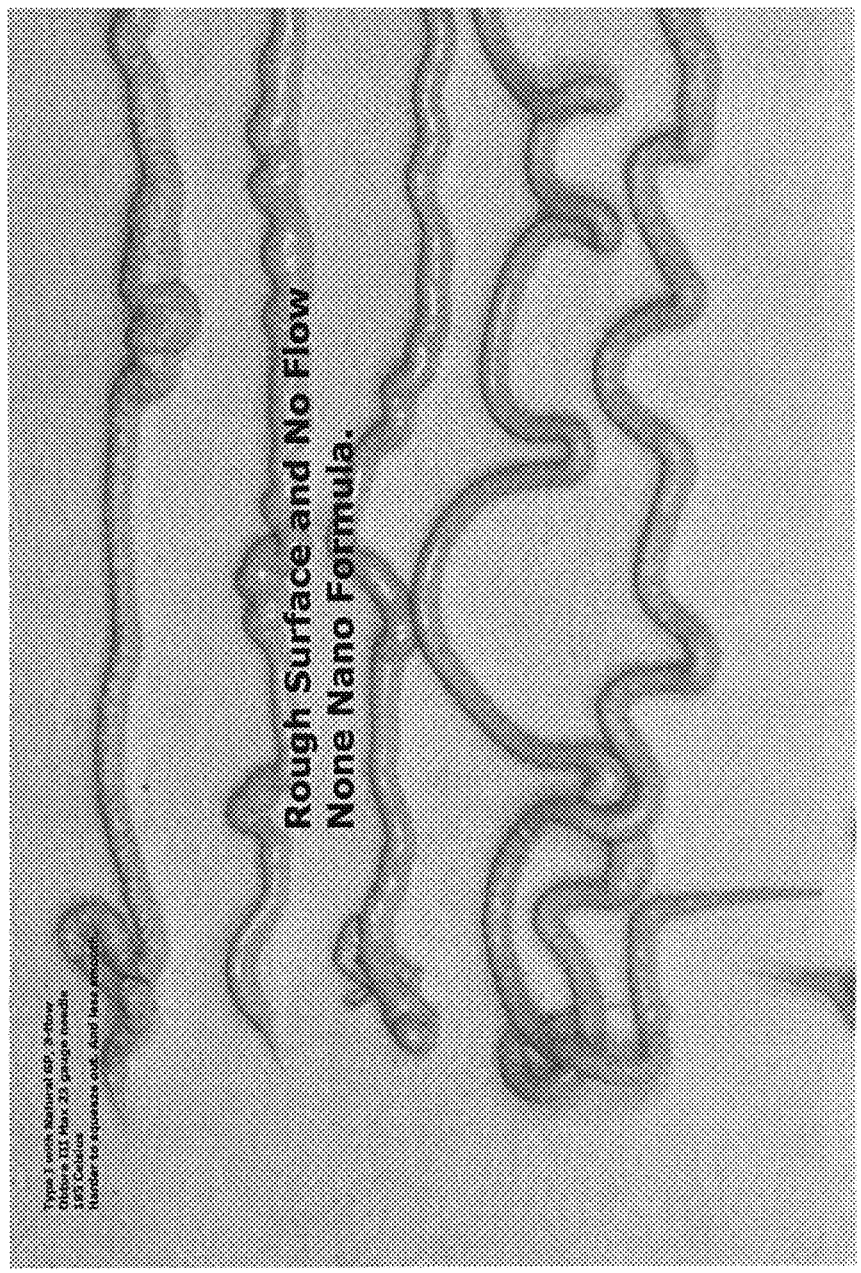
FIG. 9 illustrates rough surface for conventional filling material.

Further, when nanoparticles are added into dental Gutta Percha compound, the compound surface area is greatly increased. This produces not just a smoother surface for better flowability (less viscosity), it also gives more even flow across different temperature range FIGS. 6 and 7 show the inventive root canal filling material (Gutta Percha having nanoparticles) have more consistent flow when under heat and pressure treatment. FIG. 6 shows the mass flow rate (mg/s) and FIG. 7 shows the volumetric flow rate (microliter/s), varying with temperature, for a conventional ("Non-Nano") filling material and the inventive "Nano" filling material. FIGS. 8 and 9 show the surface textures of the inventive root canal filling material (Gutta Percha having nanoparticles) (FIG. 8) and a conventional Gutta Percha material (FIG. 9) after extruded under heat with a device used in dental clinic, which is known as Obtura III-Max. It shows in FIG. 9 the conventional Gutta Percha material has a much rougher surface texture, indicating less flowability and less ideal mixing.

Because added metallic and non-metallic nanoparticles increases heat conductivity, Gutta Percha compounding time may be reduced by about 30%. This will subject Gutta Percha material to less heat treatment and improve productivity as well.

In one embodiment, the present invention provides a root canal filling material, comprising: a matrix comprising a heat flowable material; and heat conductive particles of submicron size dispersed in the heat flowable material of the matrix, wherein the particles are nanoparticles and the nanoparticles are present in an amount of about 1 to 5% weight of the material. In one specific example, the silver nanoparticles are dispersed/distributed substantially uniform or homogeneous in the matrix of dental Gutta Percha material. The amount of silver nanoparticles added is about 0.1% to 5% by weight of the dental Gutta Percha material. In general, for the same amount (e.g., weight %) of particles, the smaller the metallic particles, the better the heat conductivity. Nano sized metallic particles are mixed into Gutta Percha material at its initial molecule breaking up stage when small dose of mild acid is being added to facilitate the breaking up process. This will ensure that nano sized metallic particles are uniformly dispersed and trapped into Gutta Percha molecules. Preferably, this should be done prior to adding any other ingredients into Gutta Percha and should be done under temperature control under about 180 degrees F. With this amount of nanoparticles in the dental Gutta Percha material, the heat conductivity of the overall root canal filler point is increased by at least 50%, and the applied operating temperature of the dentist's heating tool can be significantly reduced (e.g. by about 50% degrees C.). Other amount of metallic and non-metallic nanoparticles may be used without departing from the scope and spirit of the present invention, to achieve different desired temperature characteristics. This newly developed dental Gutta Percha formulating process with nano technology is particularly important when trying to break down (reduce) Gutta Percha molecule chain size to produce higher flowability (lower viscosity). By adding nano particles, dental Gutta Percha formulating temperature and time are reduced. More Gutta Percha molecule chains are preserved as matrix. And less or no wax is required to be added, which produces less air bubbles or voids in the filling material when subjected to heating cycles.

In an alternate embodiment, the silver nanoparticles are dispersed in manner to provide a desired density profile within the root canal filler point. For example, the nanoparticles are at higher density closer to the smaller end (apex end) of the point compared to the larger end, so as to provide a desired heating profile to flow the dental Gutta Percha material to fill the root canal during the root canal treatment procedure.

The root canal filling points can be made with the inventive filling material having metallic and non-metallic nanoparticles described above, using traditional roll processes or using the inventive injection molding process disclosed in U.S. Provisional Patent Application Nos. 61/764,927 and 61/764,935, which are incorporated by reference herein.

Instead of forming pre-shaped dental root canal filling cones (or points) with the inventive root canal filling material, the inventive filling material may be provided in bulk (e.g., pellet form) for use with an injection tool that heats and injects softened filling material directly into root canal cavities.

It is believed that by mixing metallic or non-metallic nanoparticles into dental Gutta Percha material, the root canal filler points that are ultimately formed would achieve favorable clinical effects. The Gutta Percha root canal filler point can be softened to mold it into a perfect 3-D plug to fill and seal the root canal apex area.

While the present invention has been described above in connection with the embodiment of silver nanoparticles mixed into dental Gutta Percha material, the scope of patent invention covers all possible present and future metallic and non-metallic nanoparticles mixed into dental Gutta Percha material or other types of base matrix materials suitable for root canal sealing.

I claim:

1. A root canal filling material, comprising: a matrix comprising
   a heat flowable material, wherein the heat flowable material is an trans-polyisoprene based material; and
   heat conductive particles dispersed in the heat flowable material of the matrix, wherein the size of the particles is about 0.5 to less than 1 micron.

2. The material as in claim 1, wherein the particles are metallic.

3. The material as in claim 2, wherein the particles comprise silver.

4. The material as in claim 1, wherein the particles are non-metallic.

5. The material as in claim 4, wherein the particles comprise zinc oxide or graphite.

6. The material as in claim 1, wherein the particles are about 0.1 to 5% weight of the material.

7. The material as in claim 1, wherein the particles has heat conductivity higher than heat conductivity of the heat flowable material.

8. A root canal filling cone, comprising the root canal filling material of claim 1, the cone having a taper angle ranging from 5-10 degrees.

9. The material as in claim 2, wherein the particles are selected from the group consisting of titanium and gold.

10. The material as in claim 4, wherein the particles are selected from the group consisting of diamond and Magnesium Silicate.

* * * * *